US006087327A

United States Patent [19]
Pearce et al.

[11] Patent Number: 6,087,327

[45] **Date of Patent: *Jul. 11, 2000**

[54] COMPOSITIONS AND METHODS FOR CHEMODENERVATION USING NEUROTOXINS

[76] Inventors: L. Bruce Pearce, 16 Partridge Cir., Hudson, N.H. 03051; Eric R. First, 52 N St. South, Boston, Mass. 02127-2305

[ * ] Notice: This patent issued on a continued prosecution application filed under 37 CFR 1.53(d), and is subject to the twenty year patent term provisions of 35 U.S.C. 154(a)(2).

[21] Appl. No.: 09/016,123

[22] Filed: Jan. 30, 1998

Related U.S. Application Data

[63] Continuation of application No. 08/465,767, Jun. 6, 1995, abandoned.

[51] Int. Cl.[7] .................................................... A61K 38/16

[52] U.S. Cl. .................................................... 514/2; 514/12

[58] Field of Search ............................ 514/2, 8, 12, 906; 530/350.825; 424/239.1

[56] References Cited

U.S. PATENT DOCUMENTS

| | | | |
|---|---|---|---|
| 5,183,462 | 2/1993 | Borodic | 604/51 |
| 5,298,019 | 3/1994 | Borodic | 604/51 |
| 5,401,243 | 3/1995 | Borodic | 604/51 |
| 5,512,547 | 4/1996 | Johnson et al. | 514/21 |
| 5,562,907 | 10/1996 | Arnon | 424/236.1 |
| 5,696,077 | 12/1997 | Johnson et al. | 514/2 |

FOREIGN PATENT DOCUMENTS

| | | |
|---|---|---|
| WO94/00481 | 1/1994 | WIPO . |
| WO94/28922 | 12/1994 | WIPO . |
| WO94/28923 | 12/1994 | WIPO . |

OTHER PUBLICATIONS

Bandyopadhyay et al. (1987) "Role of the Heavy and Light Chains of Botulinum Neurotoxin In Neuromuscular Paralysis," *J. Biol. Chem.* 262:2660–2663.

Black et al. (1986) "Interaction of $^{125}$I–Labeled Botulinum Neurotoxins with Nerve Terminals. II. Autoradiographic Evidence for Its Uptake into Motor Nerves by Acceptor–Mediated Endocytosis," *J. Cell Biol.* 103:535–544.

Borodic et al. (1993) "Botulinum B Toxin As An Alternative to Botulinum A Toxin: A Histologic Study," *Opthal. Plastic and Recons. Surg.* 9: 182–190.

Gansel et al. (1987) "Distinct Sites of Action of Clostridial Neurotoxins Revealed By Double–Poisoning of Mouse Motor Nerve Terminals," *Pflügers Arch.* 409: 533–539.

International Search Report of International Application No. PCT/US96/08534 (Sep. 20, 1996).

Jankovic, Joseph (1994) "Botulinum Toxin In Movement Disorders," *Curr. Opin. Neur.* 7: 358–366.

Jankovic et al. (1991) "Therapeutic Uses of Botulinum Toxin," *N. E. J. Med* 324: 1186–1194.

Jankovic, J., "Therapy With Botulinum Toxin" (1994), Jankovic and Hallett eds., Marcel Dekker, Inc., New York, NY, Forward pp. vii–ix.

Maisey et al. (1988) "Involvment of the Constituent Chains of Botulinum Neurotoxins A and B in the Blockade of Neurotransmitter Release," *Eur. J. Biochem* 177: 683–691.

(List continued on next page.)

*Primary Examiner*—Jeffrey E. Russel

*Attorney, Agent, or Firm*—Nutter, McClennen & Fish LLP; Thomas J. Engellenner

[57] ABSTRACT

The compositions and methods disclosed herein utilize admixtures of neurotoxins to cause denervation which is unexpectedly more localized and of longer duration than otherwise occurs with single neurotoxins. The compositions and methods of the invention utilize neurotoxin admixtures calibrated in median paralysis units rather than $LD_{50}$s. Admixtures of neurotoxins include, but are not limited to, the botulinum serotypes A–G and tetanus toxin. The clinical benefits of the disclosed invention include: lengthening intervals between neurotoxin treatments; reducing adverse immunogenic responses to neurotoxins; and, reducing adverse diffusion-dependent side-effects of neurotoxin treatments.

23 Claims, 5 Drawing Sheets

OTHER PUBLICATIONS

Pearce et al. (1994), "Measurement of Botulinum Toxin Activity: Evaluation of the Lethality Assay," *Toxicol. and Applied Pharmacol.* 128: 69–77.

Pearce et al. (1995), "The Median Paralysis Unit: A More Pharmacologically Relevant Unit of Biologic Activity for Botulinum Toxin," *Toxicon* 33: 217–227.

Poulain et al. (1991) "Heterologous Combinations of Heavy and Light Chains From Botulinum Neurotoxin A and Tetanus Toxin Inhibit Neurotransmitter Release in Aplysia," *J. of Biol. Chem.* 266: 9580–9585.

Schantz et al. (1992) "Properties and Use of Botulinum Toxin and Other Microbial Neurotoxins in Medicine," *Microbiol. Rev.* 56: 80–99.

Sudhof, T.C. (1995) "The synaptic vesicle cycle: a cascade of protein–protein interactions", Nature 375: 645–653.

NEUROTOXIN A
MPU

NEUROTOXIN B
MPU

NEUROTOXIN A+B
MPU (TOTAL)

DAYS

FIG. 1

COMPOSITIONS AND METHODS FOR CHEMODENERVATION USING NEUROTOXINS

This application is a continuation of U.S. Ser. No. 08/465,767, filed Jun. 6, 1995, now abandoned, the entire disclosure of which is incorporated herein by reference.

FIELD OF THE INVENTION

The present invention relates generally to compositions and methods for chemodenervation using admixtures of neurotoxin.

BACKGROUND OF THE INVENTION

Botulinum neurotoxin is a Clostridial neurotoxin that produces flaccid paralysis by irreversibly inhibiting the release of acetylcholine (ACh) from nerve terminals at the motor endplate. While this ACh-related phenomenon has been well documented and is generally considered its primary mechanism of action, numerous researchers have evidence that botulinum neurotoxins may also act by impairing or inhibiting vesicular release of other neurotransmitters and/or neuroactive substances. See, e.g., Ashton et al. (1988) 50 *J.Neurochemistry* 1808; McMahon et al. 267 *J.Biol.Chem.* 21388; Blasi et al. (1994) 88 *J.Physiol.* 235.

The profound specificity of action of botulinum neurotoxin has contributed to the fact that this neurotoxin has become widely employed for its therapeutic potential in the treatment of a variety of involuntary movement disorders (Borodic et al. (1991), 4 *Opthalmology Clinics of North America* 491–504; Hambelton, P. (1992), 239 *J. Neurol.* 16–20; Schantz et al. (1992), 50 *Microbiol. Rev.* 1:80–99; Valtorta et al. (1993), 27 *Pharmacol. Res.* 1:33–44). Intramuscular injection of nanogram quantities of purified botulinum neurotoxin is the treatment of choice for a number of clinical indications including: blepharospasm, spasmodic dysphonia, hemifacial spasm, and adult onset spasmodic torticollis. Botulinum neurotoxin therapy has primarily involved intramuscular injection of the serotype A, however, the F and B serotypes are currently also considered clinically relevant (Greene et al. (1993), *Botulinum and Tetanus Neuroneurotoxins* (ed. B. R. DasGupta, Plenum Press, New York pp. 651–654). These additional serotypes hold the promise of alternative therapies for patients that develop resistance to the A neurotoxin. Moreover, these neurotoxins may also possess intrinsic properties that result in significant therapeutic advantages.

Botulinum serotype A and B neurotoxins exhibit a number of functional, structural, and mechanistic similarities. Both produce chemical denervation at the neuromuscular junction that appears to occur through a three step process resulting in inhibition of normal neurotransmitter release (Schmitt et al. (1981) 317 *Naunyn-Schmiedeberg's Arch. Pharmacol.* 326–330; Simpson, L. L. (1981) 33 *Pharmacol. Rev.* 155–158). Both species have a molecular weight of approximately 150,000 daltons, and the active form of the neurotoxin exists as a dimeric molecule consisting of a light (approximately 50,000 DA molecular weight) and heavy (approximately 100,000 DA molecular weight) subunit linked by a disulfide bond (Simpson, L. L. (1981) 33 *Pharmacol. Rev.* 155–158; Tse et al. (1982) 122 *Eur. J. Biochem.* 493–500).

Despite the general similarities between the A and B neurotoxins, however, closer examination of these species reveals very significant differences. For example, all of the neurotoxins produced by C. botulinum are immunologically distinct which suggests significant differences in their amino acid sequences. Analysis of the partial amino acid sequences for the A and B serotypes has revealed greater homologies between the primary and secondary structure for the light subunit chains than the heavy subunit chains. The degree of primary structure homology is only 20% for the light subunit chains versus 40% for the heavy (Evans et al. (1986) *Eur. J. Biochem.* 409–416). Although similar in secondary and tertiary structure, differences in the conformation of the neurotoxins at or near the active site may be responsible for the differences in neurotoxicity (Dasgupta, B. R. (1990) 84 *J. Physiol. (Paris)* 220–228).

Electrophysiological studies have demonstrated that botulinum neurotoxins affect different steps in the neurotransmitter release process. Botulinum serotype B affects synchronization of quantal transmitter release whereas serotype A does not (Singh et al. (1989) 86 *Mol. Cel. Biochem.* 87–95). Similarly, differences exist with regard to reversibility of the inhibition of calcium-dependent release of neurotransmitter. Introduction of calcium into nerve terminals using a calcium ionophore produces the release of transmitter from synaptosomes poisoned by serotype A more readily than those poisoned by serotype B (Molgo et al. (1990) 84 *J. Physiol. (Paris)* 152–166). At the neuromuscular junction, aminopyridine was also more effective at reversal of inhibition produced by botulinum neurotoxin A (Ashton et al. (1991) 56 *J. Neurochem.* 827–835). Ashton et al. (1991) have demonstrated that microtubule-dissociating drugs were effective in blocking the inhibitory effects of serotype B on neurotransmitter release and ineffective against the serotype A neurotoxin.

The differences in the toxic and neurophysiological effects of the serotype A and B neurotoxins may be related to the putative existence of two distinct receptor (acceptor) sites for these species (Singh et al. (1989) 86 *Mol. Cel. Biochem.* 87–95). Examination of the effect of botulinum neurotoxin A on $^{125}$I-botulinum neurotoxin B binding to neuronal membranes showed a very weak interaction involving both the high and low affinity sites for toxin binding.

Pearce et al. (1995) in 33 *Toxicon* 217 and Pearce et al. (1994) in 128 *Toxicol. App. Pharmacology* 69 have recently reported that a regional chemodenervation assay, which does not rely on the conventional $LD_{50}$ calibration standard, more accurately predicts the clinical potency of botulinum neurotoxins. As disclosed by Pearce et al., this assay is useful to quantify more accurately the denervating potential of injections of individual botulinum neurotoxins. On the one hand, such injections of individual botulinum neurotoxins have proven clinically useful in creating regional muscular denervation to treat segmental movement diseases in man. On the other hand, however, one of the limitations of such traditional clinical therapy is that the individual neurotoxin must be repetitively injected into muscles every 10–14 weeks to effectively treat these chronic movement diseases. Some researchers have sought alternatives such as more potent preparations of neurotoxins which have demonstrated some clinical efficacy in animals. In contrast, other alternatives using conventionally calibrated doses of combinations of serotypes A and B have failed (*In Therapy with Botulinum Toxin* (1994) (ed., J. Jankovic and M. Hallett; Marcel Dekker, Inc., N.Y.)pp. vii–ix).

Clinically speaking, what is needed is a composition and a method which (a) act by increasing the duration of action of the chemodenervating agent so that repetitive injections can be given less often than the traditional clinical protocol currently prescribes; (b) are effective at dosage amounts which are less likely to stimulate a patient's immunogenic responses; and (c) accomplish the aforementioned clinical objectives with no or minimal adverse diffusion-dependent side-effects typically observed with prior art compositions and methods.

It is an object of this invention to provide compositions and methods which unexpectedly increase the beneficial effects derived from botulinum-based chemodenervation. It is a further object of the present invention to provide compositions and methods which utilize certain admixtures of neurotoxins to achieve potentiation of the temporal duration of chemodenervation which has heretofore been undescribed. It is another object of the present invention to provide certain compositions and methods which further permit more localized chemodenervation using admixtures of neurotoxins which contain lesser amounts of individual neurotoxins than heretofore has been described. It is yet another object of this invention to provide compositions and methods which further permit more localized chemodenervation using admixtures of neurotoxins which produce fewer diffusion-dependent side effects.

SUMMARY OF THE INVENTION

The present invention provides improved compositions and methods for localized, regional denervation. Specifically, the present invention provides compositions, and methods of use thereof, characterized by an enhanced specificity of denervating effects. The instant compositions comprise admixtures of neurotoxins that cause more localized, longer lasting denervation than heretofore described. The features and benefits of the instant compositions, and methods of use thereof, will be best understood and appreciated by reference to FIG. 1.

FIG. 1 depicts both the extent of and the duration of denervation achieved using certain exemplary admixtures of neurotoxins in accordance with the instant invention. In all three panels, the horizontal axes depict duration of denervation in days, while the vertical axes depict dosage amounts of individual or admixed botulinum neurotoxin serotypes. The top and middle panels depict the denervating effects observed upon administration of 1 MPU (median paralysis unit) or 2 MPU of neurotoxin serotype A or B, respectively; the bottom panel depicts the denervating effects observed upon administration of 2 MPU of exemplary admixtures of neurotoxin serotypes A and B (1 MPU each of neurotoxin A and B). In all three panels, the extent of denervation is schematically depicted as concentric circles. Localized or regional denervation, as defined herein, is represented by the inner, solid circle; in contrast, spreading or non-localized, diffusion-dependent denervation is represented by the cross-hatched circle. For purposes of this discussion, it is assumed that the point of administration of a single neurotoxin or an admixture of neurotoxins is always in the center of the solid circle.

Upon a comparison of the denervating effects depicted in FIG. 1, it is apparent that an admixture of 2 MPU of neurotoxins A and B exhibits characteristics related to both duration and extent distinguishable from either neurotoxin alone. When administered at 2 MPU, for example, neither neurotoxin A or B can cause only localized denervation for approximately 17 days; at 2 MPU, neurotoxin A or B can only cause non-localized, wider spread denervation for 17 days. At 1 MPU, both neurotoxin A and B can, in fact, cause more localized, less widespread denervation, but it persists for only approximately 8–9 days.

In contrast, for example, 2 MPU of an admixture of neurotoxin A and B (1 MPU A and 1 MPU B) causes more localized, less widespread denervation which persists for approximately 17 days. Thus, an admixture can prolong denervation yet delimit and minimize the spread of non-localized denervation. Clinically speaking, this is a particularly beneficial and advantageous feature because the desired effects of denervation therapy can now be maximized over time without exposing a patient to the undesirable and non-specific side-effects caused by diffusion-dependent spreading.

Generally speaking, the compositions and methods of the present invention improve the quality of botulinum neurotoxin-based agents currently used in clinical medicine by:

1. Increasing the duration of chemodenervating action, thereby achieving a clinically beneficial result using fewer injections.
2. Providing longer intervals between injections, thereby reducing antigenicity. Antigenicity and resistance have been directly related to both the number and frequency of neurotoxin injections. Increasing the duration of chemodenervating action decreases the potential of an adverse immunogenic response.
3. Permitting a reduction in the mass of a particular neurotoxin serotype used in drug formulation, thereby reducing antigenicity. Increased neurotoxin serotype mass, when used to formulate clinical preparations, directly correlates with antibody development, thereby ultimately rendering such preparations clinically ineffective. A method of reducing the neurotoxin mass of an individual serotype in the formulation represents a partial solution to this troublesome therapeutic problem.
4. Permitting sustained denervation within the injected muscle. Regional denervation represents a major mechanism of action by which botulinum neurotoxins can render a beneficial clinical effect. The unexpected potentiation disclosed herein manifests one such benefit with respect to regional chemodenervation. Such an effect is instrumental in achieving enhanced therapeutic results in muscle regions being treated.

For example, as disclosed herein and depicted in FIG. 1, there are significant unexpected advantages associated with specifically admixing neurotoxins in chemodenervating formulations. As disclosed herein, these advantages are clearly demonstrable using the mouse hind limb paralysis model and dosages of neurotoxins calibrated using the median paralysis unit (MPU) calibration standard. Intramuscular injection of admixtures of botulinum A and B neurotoxins results in a localized regional denervation that does not display the degree of diffusion-dependent effects produced at equivalent doses of either toxin alone; additionally, this localized regional denervation endures for a longer period of time. Thus, when administered in accordance with the median paralysis unit dose standard, intramuscular injection of admixtures of A and B neurotoxins results in a more localized, focused and longer-lasting denervation than possible with either serotype alone.

Accordingly, in one aspect, the present invention provides a composition for localized chemodenervation which comprises an admixture of a first neurotoxin, a second neurotoxin and a pharmaceutically-acceptable excipient. The neurotoxins are admixed in amounts relative to each other such that the composition causes more localized, longer lasting denervation than heretofore described. In all embodiments of the instant invention, the neurotoxins are calibrated using median paralysis units. The composition disclosed herein can further comprise a third neurotoxin.

In some currently preferred embodiments, the first neurotoxin is selected from, but not limited to, the group of neurotoxins including C. botulinum serotype A, B, C, D, E, F, and G. In certain embodiments, the first neurotoxin is serotype A. In some currently preferred embodiments, the second neurotoxin is selected from, but not limited to, the group of neurotoxins including C. botulinum serotype A, B, C, D, E, F and G. In certain embodiments, the second neurotoxin is serotype B. In yet other embodiments, the second neurotoxin is tetanus toxin.

The instant invention further contemplates a composition comprising an admixture of a first neurotoxin, a second neurotoxin and a pharmaceutically-acceptable excipient wherein the neurotoxins are admixed in amounts relative to each other such that the composition causes more localized denervation than heretofore described. In certain other embodiments, the invention contemplates that the composition causes longer lasting denervation.

In another aspect, the instant invention provides a method for localized chemodenervation of a muscle involving administering to a muscle a dosage of a pharmaceutical composition sufficient to cause localized denervation. The composition of the instant method comprises an admixture of a first neurotoxin, a second neurotoxin, and a pharmaceutically-acceptable excipient. Administration of this composition in accordance with the method of the instant invention causes more localized, longer lasting denervation.

In another embodiment, the method further involves administering a unit dosage of the composition of the instant invention to an innervation zone within a volume of muscle comprising a single muscle. All embodiments of the instant invention contemplate administering dosages calibrated using the median paralysis unit calibration standard.

The instant invention further contemplates that practice of certain embodiments of the method causes more localized denervation than would occur by administering one or the other neurotoxin alone. In certain other embodiments, the invention contemplates that practice of the method causes longer lasting denervation than would occur by administering one or the other neurotoxin alone.

As disclosed herein, the invention further provides an improved method of locally diminishing spasm and involuntary contraction in a muscle involving administering the composition of the instant invention into at least a portion of an innervation zone of a muscle. In yet another embodiment, the instant invention provides an improved method of locally diminishing tremor, rigidity or spasicity in a muscle involving administering the composition of the instant invention into at least a portion of an innervation zone of a muscle.

These and other objects, along with advantages and features of the invention disclosed herein, will be apparent from the description, drawings and claims that follow.

BRIEF DESCRIPTION OF FIGURES

The foregoing and other objects, features and advantages of the present invention, as well as the invention itself, will be more fully understood from the following description of preferred embodiments, when read together with the accompanying drawings, in which:

FIG. 1 is a comparative depiction of the denervating characteristics of certain exemplary admixtures of neurotoxins versus neurotoxins alone.

DETAILED DESCRIPTION OF THE PREFERRED EMBODIMENTS

Figure 2:
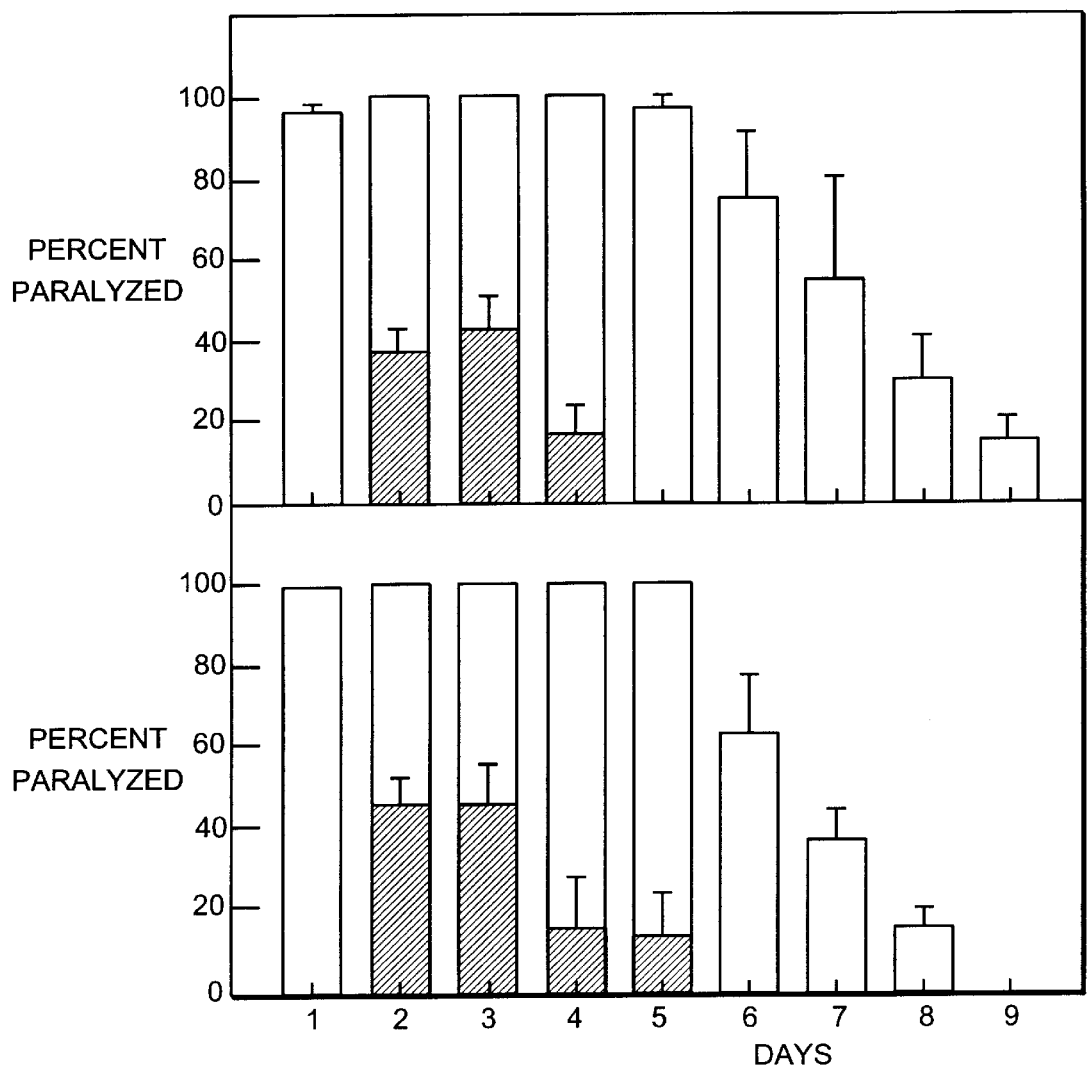
FIG. 2 is a bar graph illustrating a comparison of the effects of A (upper panel) and B (lower panel) neurotoxins on paw (open bars) versus hind limb (solid bars) paralysis.

As will be described below in greater detail, the instant invention relates to compositions and methods for chemodenervation. Specifically, the compositions and methods relate to localized chemodenervation caused by admixtures of neurotoxins. In one aspect, the instant compositions are effective to cause denervation which is more localized and longer lasting than heretofore demonstrated or appreciated by the prior art. In another embodiment, the compositions are effective to cause denervation for a longer duration while still other embodiments are effective to cause more localized denervation. Other embodiments of the instant compositions are effective to diminish spasm, involuntary contraction, tremor rigidity and/or spasicity for a longer duration of time. In another aspect, the method of the instant invention causes more localized chemodenervation by administration of neurotoxin admixtures. In a currently preferred embodiment, the instant method causes more localized denervation for a longer duration than heretofore possible with single neurotoxins. In another embodiment, the method uses neurotoxin admixtures to cause more localized denervation, while in still other embodiments the method causes longer lasting denervation.

As used herein, the terms "localized chemodenervation" and "localized denervation" mean denervation of a particular anatomical region, usually a muscle or group of anatomically- and/or physiologically-related muscles, which results from administration of a chemodenervating agent, for example a neurotoxin, to the particular anatomical region. The term "regional denervation" as used herein is also intended to have a similar meaning.

As used herein, the term "neurotoxin" is intended to mean any neurotoxic substance suitable for use in the instant invention. As will be understood by the skilled practitioner, neurotoxic substances suitable for use include chemodenervating agents capable of interrupting normal physiological function at a neuromuscular junction, for example, or other neuroeffector site. For example, substances which interrupt nerve impulse transmission across the neuromuscular junction are suitable for use. Similarly, substances which impair vesicular release of neuroactive substances, such as neurotransmitters and neuropeptides, are suitable for use. It is contemplated that any neuronally-released substance that normally modulates neuromuscular activity or participates in related feedback mechanisms can be affected by the compositions and methods disclosed herein. Many chemodenervating agents having these properties are well-known in the art, and the skilled artisan will be able to identify them, as well as their equivalents, using only routine experimentation.

According to one embodiment of the instant invention, the composition comprises a first neurotoxin, a second neurotoxin, and a pharmaceutically-acceptable excipient. In another embodiment, the invention further contemplates a composition comprising a third neurotoxin. Currently preferred neurotoxins include, but are not limited to, the neurotoxins of C.botulinum. As is well-known in the art, there are seven immunologically distinct serotypes of botulinum neurotoxins designated serotypes A–G. It is also well-known that the different serotypes share structurally homologous subunits. Botulinum neurotoxins are first synthesized as 150,000 molecular weight polypeptides known in the art as protoxins which are subsequently processed by proteolytic enzymes into a heavy chain subunit (approximately 100,000 molecular weight) and a light chain subunit (approximately 50,000 molecular weight). The biologically active botulinum neurotoxin consists of one light and one heavy chain subunit bound by a disulfide bond. Some reports suggest that botulinum neurotoxins are folded into several three-dimensional domains having distinct functions within the chemodenervating process.

Among the botulinum serotypes, serotypes A and B are particularly preferred. Serotype A neurotoxin is commercially available in pharmaceutically-acceptable grade from: Allergan Pharmaceuticals, Inc. (Irvine, Calif.) under the tradename OCULINUM™, now known by the tradename Botox™; and, Porton Down Ltd. (U.K.) under the tradename Dysport™. Serotype A neurotoxin can also be prepared using techniques well-known in the art. For example, materials and methods suitable for the preparation of botulinum neurotoxin A are disclosed in pending U.S. Pat. No. 5,696,077, the disclosure of which is hereby incorporated by reference.

As also described in U.S. Pat. No. 5,696,077, stable pharmaceutically-acceptable preparations of botulinum neurotoxin B can be prepared for use in the instant compositions and methods. Briefly, preparations of botulinum neurotoxin B suitable for use herein are those in which the purified neurotoxin is combined with a complex of non-toxic botulinum-derived proteins and excipient. In one embodiment, neurotoxin B is associated with a botulinum-derived red blood cell agglutinating factor co-expressed with the neurotoxin by C.botulinum. As described in U.S. Pat. No. 5,696,077, a preferred complex formed from type B neurotoxin and at least one protein has a molecular weight of about 300,000 (the M complex). Another preferred complex formed from type B neurotoxin and at least two proteins has a molecular weight of about 450,000 (the L complex). These complexes are currently preferred due to their superior stability and potency compared to non-complexed neurotoxin B. Type B neurotoxin isolated from C.botulinum generally occurs as a mixture of L and M complexes. Botulinum B neurotoxin is also available commercially from Interactive Biologics Associates (Cambridge, Mass.) formerly Associated Synapse Biologics (Boston, Mass.).

Other currently preferred neurotoxins include those isolated from C.tetani. As is well-known in the art, tetanus toxin resembles botulinum neurotoxin in its structure and mode of action under certain conditions. It has been reported that these neurotoxins have significant homology at the amino-terminus of the heavy and light chain subunits. Some botulinum serotypes cross-react immunologically with tetanus toxin. Tetanus toxin can be prepared using materials and methods well-known in the prior art. Using only routine experimentation, the skilled artisan can obtain tetanus neurotoxin in quantities and of a quality suitable for use as disclosed herein.

The instant invention also contemplates that the term "neurotoxin" further includes a neurotoxin "subunit." For example, the botulinum neurotoxins are composed of subunits as described above. After treatment with a di-sulfide bond disrupting agent, the subunits can be separated by conventional techniques such as chromatography. It is contemplated that neurotoxin subunits, or modified versions thereof, can be combined with certain other moieties, such as stabilizers and/or toxicity enhancers, for use as described herein. The instant invention also contemplates that the term "neurotoxin" includes a neurotoxin "fragment," e.g., a portion(s) of neurotoxin which retains neurotoxic and/or biological activity. The term "neurotoxin" also contemplates neurotoxic substances which share amino acid sequence homologies and/or identities with currently known neurotoxins, the identification of which will be routinely ascertained by the skilled artisan. Other suitable neurotoxins include neurotoxin "chimeras." The above-described isolated subunits from different botulinum serotypes, for example, can be reassociated to form neurotoxic, biologically-active chimeras. Similarly, neurotoxic chimeras can be formed between botulinum neurotoxins subunits and tetanus toxin subunits. As used herein, the term "chimera" also contemplates subunits from other toxic substances such as, for example, ricin.

The above-defined neurotoxins suitable for use with the instant invention can be naturally-occurring or can be synthetically produced using recombinant DNA technologies and/or in vitro protein synthesizing techniques well known in the art. Synthetically produced neurotoxins are also intended to include substances which have been rendered neurotoxic by a variety of manipulations, such as enzymatic or chemical processing and conjugation or derivatization with moieties which themselves are neurotoxic. Again, identification of equivalents will be within the skill of the ordinary practitioner using only routine experimentation.

As disclosed herein, the composition of the instant invention comprises a first neurotoxin, a second neurotoxin and a pharmaceutically-acceptable excipient. As used herein, "pharmaceutically-acceptable excipient" is intended to include any substance capable of being admixed and administered with the instant composition and which allows the composition to perform its intended function as disclosed herein. According to its intended meaning, an excipient is a substance which is added to a pharmaceutical composition as a vehicle or stabilizer. Excipients suitable for use include, but are not limited to, proteins such as gelatin. A currently preferred excipient is human serum albumin. It is within the skill of the ordinary practitioner using no more than routine experimentation to identify a suitable excipient for combination with a particular neurotoxin(s).

To make the composition of the present invention, the neurotoxins are further admixed with an excipient and a sterile diluent to dilute the neurotoxin to the desired amount. The presence of the excipient helps to maintain the stability of the composition during and after dilution. The diluent can be any pharmaceutically-acceptable material which will not adversely affect the stability of the composition, such as for example, sterile saline, physiological buffer or water. Guidelines for suitable dilution practices are set forth in U.S. Pat. No. 5,696,077, previously incorporated herein by reference.

As disclosed in detail in above-referenced U.S. Pat. No. 5,696,077, excipient is preferably used at a concentration sufficient to provide solution stability to the complex during and after dilution, and to retain the desired activity level upon lyophilization and reconsistution. The excipient also ensures that the toxin does not adhere to glass. As will be obvious to the skilled artisan, the particular concentration needed to accomplish these goals will depend in part upon the particular excipient selected for use. No more than routine experimentation will be required.

In a currently preferred embodiment, the composition is in a substantially water-free configuration. For example, the above-described composition can be dried for storage an/or shipping, if desired, and subsequently reconstituted. Drying is currently preferably accomplished by lyophilization as disclosed in the above-referenced U.S. Pat. No. 5,696,077. Any means of accomplishing a substantially water-free configuration which does not impair or compromise the integrity of the composition is contemplated for use herein. Identification of such a process is within the skill of the ordinary practitioner.

The instant invention contemplates any mode of administration which is suitable for locally administering a pharmaceutical composition, including for example, transdermal diffusion, transcutaneous injection, intramuscular injection, and implantation of a depot-type release modality which releases the pharmaceutical composition into the selected area. As disclosed herein, a currently preferred mode of administration is intramuscular (i.m.) usually, but not necessarily limited to, direct injection into the muscle using a fine gauge needle under electromyographic control.

Other routes of administration are contemplated as suitable, especially given the phenomenon of neurotoxin diffusion described herein. For example, routes of administration which may also lead to diffusion of toxin to clinically significant sites of action include parenteral (for regional administration), oral, subcutaneous injection, rectal and topical administration.

In the case of subcutaneous or depot-type administration, botulinum neurotoxin admixture is suspended in normal phosphate buffer pH 6.5 containing gelatin stabilizer and administered subcutaneously (0.1 ml) in the gastrocnemius muscle of a mouse, for example. Similarly, neurotoxin admixture can be delivered by implanting a suitable depot preparation of the neurotoxins which dissolves gradually releasing the admixture in a constant fashion. It is contemplated that the neurotoxin would diffuse to the neuromuscular junctions resulting in inhibition of ACh release, for example, and at sufficiently high dosages complete paralysis of the muscle would occur. The effects of such administration of neurotoxin can be monitored using the degree of paralysis of the hind limb on the day of peak paralysis as disclosed herein. Specifically, in a quantal assay such as the hind limb paralysis assay described herein, the percentage of mice showing complete paralysis can be determined. Probit analysis as described below can be performed on these quantal data obtained for a range of concentrations of the neurotoxin injected and an $ED_{50}$ (median effective dose) determined as also described below.

In the case of topical administration, the effects of such administration can be monitored as follows. Botulinum neurotoxin, alone or admixtures thereof, is solubilized in normal phosphate buffer pH 6.5 containing gelatin stabilizer and administered topically by soaking a sterile cotton ball with 0.2 ml of neurotoxin preparation and inserting this into the nasal cavity of a dog, for example. The inhibitory effect of the neurotoxins on neurotransmitter release from the autonomic nerves innervating the glands in the nose can then be determined by measuring nasal secretions (rhinorrhea) produced following electrical stimulation of the sphenopalatine ganglion. (See, e.g.,. Shaari et al. (1995) 112 *Otolaryngol. Head Neck Surg.* 566.)

It has been reported that numerous such modes of administration can be efficacious to interrupt vesicular release of a variety of neuroactive substances such as neurotransmitters and neuropeptides. Using the compositions of the instant invention, it is now possible to further measure other possible neurotoxin effects on neuroactive substances. For example, inhibition of the release of various neurotransmitters and neuropeptides by the compositions of the instant invention can be measured using prior art brain slice or synaptosome assays. Brain slices can be incubated with admixtures of botulinum neurotoxin in normal Krebs buffer at 37° C. under 95% $O_2$/5% $CO_2$ and the presence of radiolabelled precursors for neurotransmitters or the neurotransmitter for 120 minutes. The slices are then removed from the incubation and superfused with normal Krebs and exposed to Krebs buffer containing 30 mM KCl to stimulate the release of neurotransmitter. Under these conditions, it will be possible to measure the effect of pretreatment with admixtures of botulinum neurotoxins on depolarization-evoked release of a variety of neurotransmitters (e.g.,NE, DA, 5-HT, Gly, Glu,) from brain. Published studies have shown that single botulinum neurotoxins inhibit the release of all transmitters studied.

Similarly, the compositions of the instant invention can be used to measure inhibition of the release of neuropeptides from motor neurons using a standard neurophysiological method similar to that described by Sala et al. (1995) in 15 *J.Neurosci.* 520. This type of experiment can provide evidence that botulinum neurotoxin admixtures inhibit the release of calcitonin gene-related peptide (CGRP) from motor nerves in rats. For example, the fibular nerve of rats can be stimulated (60 pulses, 0.2 msec) at 100 Hz every five seconds for 1 minute to 4 hours. Upon completion of the stimulation period, the muscles can be removed and examined for the content of CGRP using art-recognized immunohistological techniques. These experiments can be performed with and without local injection of sufficient admixtures of botulinum neurotoxins to cause complete paralysis of the hind limb of the rat. The results of this experiment will show that the depletion of CGRP caused by excessive stimulation of the motor nerve innervating the muscles of the leg is blocked by pretreatment with admixtures of botulinum toxin. Similarly, the effect of neurotoxin admixtures on release of other neuropeptides such as vasoactive intestinal peptide (VIP), Substance P (SP) and Neuropeptide Y (NY) can be studied using other animal model systems well-known in the prior art.

When practiced in accordance with the instant invention, calibration of a dosage amount is accomplished using the "median paralysis unit" (MPU), rather than the prior art's conventional dose calibration standard, the $LD_{50}$ (median lethal dose). It has been reported that using lethality as an endpoint is not an optimum measure of the therapeutically-relevant biologic activity of botulinum neurotoxin. Comparisons of neurotoxin preparations (single or admixed) using the standard LD., assay described herein and the hind limb paralysis assay described herein indicate that the $LD_{50}$ is not an accurate or adequate measure of biological potency or efficacy. As described below, the paralysis assay and the MPU calibration standard are superior to the lethality assay for assessing therapeutically-relevant biologic activity of botulinum neurotoxin preparations as contemplated herein. (See, e.g., Pearce et al. (1995) 33 *Toxicon* 217; Pearce et al. (1994) 128 *Toxicology and Applied Pharmacology* 69, the disclosures of which are hereby incorporated by reference.)

The advantage of the MPU is that it is a standardized dose of neurotoxin that produces a specific degree of regional denervation measured in terms of the paralysis observed following i.m. administration to the mouse hind limb. The MPU serves as a standardizing unit which defines the relevant denervating activity in clinically suitable preparations of neurotoxin (single or admixed). Definition of the clinical potency of botulinum neurotoxin preparations, for example, in terms of MPU is particularly useful for practice of the instant methods and compositions. Using prior art calibrated dosages of neurotoxins, practitioners failed to appreciate the clinical and therapeutic potential of combinations of botulinum serotypes A and B. See, e.g., *Therapy With Botulinum Toxin* (1994) (Jankovic and Hallett, eds.; Marcel Dekker, Inc., N.Y.) pp. vii–ix.

As disclosed herein, an effective dosage amount of the composition of the instant invention means that dosage at which more localized denervation occurs, and further means that dosage at which denervation is longer lasting. This has, in essence, been depicted schematically in FIG. 1 described above. For example, as disclosed herein, administration of a dosage of 1 MPU of neurotoxin A admixed with 1 MPU neurotoxin B results in sustained paw paralysis (as measured using the mouse hind limb paralysis assay disclosed herein) for a period of time longer than the paralysis observed when 1 MPU of neurotoxin A or 1 MPU neurotoxin B is administered singly. Furthermore, the paralysis observed upon administration of a total of 2 MPU (1 MPU neurotoxin A and 1 MPU neurotoxin B) of the instant composition is more localized and less wide-spread than is the paralysis observed upon administration of a total of 2 MPU of either neurotoxin A alone or neurotoxin B alone. As will be obvious to the skilled practitioner, the effective dosage amount can be manipulated to achieve the desired duration of denervation as well as the desired regional extent of denervation.

The composition of the instant invention overcomes a significant disadvantage typically associated with prior art neurotoxin compositions. Using prior art neurotoxin compositions, e.g., neurotoxin A or B alone, the duration of action of treatment is limited and complicated by diffusion-dependent side-effects. These adverse side-effects are minimized by the admixtures disclosed herein. The admixtures of the instant invention thus can permit administration of higher total dosages to achieve a longer lasting denervation yet spare the patient side-effects such as non-specific impairment of adjacent muscle(s).

Only routine experimentation will be required to ascertain the appropriate dosage for a particular clinical objective. As described herein and depicted in FIG. 1, an effective dosage of an admixture of neurotoxins causes denervation for longer times and within a more localized site than possible with any one of the neurotoxins alone. It will be obvious to the skilled artisan that more localized denervation such as that described herein can be further accomplished by manipulating the neurotoxin mass in an effective dosage amount and/or by adjusting the volume in which the mass is reconstituted and administered.

It is further contemplated that an effective dosage amount of the instant compositions diminishes spasm and involuntary contraction in a muscle for a longer duration of time. It is additionally contemplated that an effective dosage amount similarly diminishes tremor, rigidity or spacticity in a muscle. Moreover, the advantages of administering the instant composition in accordance with the instant method will be immediately obvious to the skilled practitioner.

EXEMPLIFICATION

Practice of the invention will be still more fully understood from the following examples, which are presented herein for illustration only and should not be construed as limiting the invention in any way.

EXAMPLE 1

Materials And Methods (a) The Hind Limb Regional Chemodenervation Assay:

Injection of botulinum A or B neurotoxin into the mouse gastrocnemius muscle resulted in a number of effects on hind limb function. Paw paralysis was observed at lower doses and was also an early partial response to injection of higher doses of neurotoxin. As used herein, "complete paw paralysis" is defined as the inability of the mouse to grip with the paw. At higher neurotoxin doses, there occurred a further progression to more generalized compromised function of the injected limb and ultimately to complete hind limb paralysis. "Complete hind limb paralysis" is defined as the complete absence of voluntary movement of the injected limb.

Accordingly, two measures of the extent of denervation are utilized herein, one is complete hind limb paralysis and the other is complete paw paralysis. As used herein, partial paralysis also means paw paralysis and complete paralysis also means hind limb paralysis.

The amount of botulinum neurotoxin in a given preparation was calibrated using two different units of biologic activity. The conventional calibration standard unit of activity for botulinum neurotoxins is the $LD_{50}$ in mice; 1.0 $LD_{50}$ is equivalent to 1.0 unit of activity. An alternative calibration unit is the median paralysis unit (MPU); as used herein, 1.0 MPU is that amount of neurotoxin which produces complete hind limb paralysis in 50% of a population of mice. The methods for determination of these units of activity are described in detail below.

(b) Determination of the Median Paralysis Unit:

Paralysis of the mouse hind limb was produced by i.m. injection of botulinum neurotoxin using an art-recognized method similar to that previously described by Pearce et al. (1994) 128 *Toxicol. App. Pharmacology* 69, and disclosed in pending U.S. Ser. No. 08/281,450, now abandoned (the disclosure of which is hereby incorporated by reference) as well as in the related disclosures of U.S. Pat. No. 5,183,462; U.S. Pat. No. 5,298,019; and U.S. Pat. No. 5,401,243, all of said disclosures hereby incorporated by reference. Briefly, neurotoxin was diluted with 0.2% gelatin in 30 mM sodium phosphate buffer, pH 6.2 and 0.1 ml of diluted neurotoxin preparations were injected into the gastrocnemius muscle of the hind limb of 18–22 g mice. Neurotoxic activity was assessed by evaluating the fraction of mice that showed complete paralysis of the right rear hind limb.

Complete paralysis was manifested as an inability of the mouse to use the right rear hind limb to support weight or to escape. Once complete paralysis occurred, the hind limb was usually held up against the body or dragged. These postures were considered cardinal signs of complete paralysis.

Five to six dilutions of neurotoxin were injected into 10 mice per dilution. Doses of neurotoxin were increased in a geometric progression by a factor of 1.25. Applying well-known statistical considerations, doses were centered on the $ED_{50}$ (median effective dose) to provide a symmetric design (Finney, D. J. (1978) *Statistical Method in Biological Assay* Charles Griffin & Co., London). To avoid bias, only doses of neurotoxin at which no death occurred prior to determining the $ED_{50}$ were utilized in the probit analysis. The percent paralyzed was determined at each dose of neurotoxin and standard probit analysis was performed on the data (Bliss, C. I. (1938) 11 *Q.J. Pharm. Pharmac.* 192–216) using the probit program provided with the statistical package, SPSS-X (SPSS, Inc., Chicago, Ill.). This program estimates the best line by regression analysis and the values for the intercept and slope are estimated by the maximum likelihood method. A standard Pearson chi-square goodness of fit test was used and, if this estimate was significant, a heterogeneity factor was then used in the calculation of the confidence limits.

The $ED_{50}$ obtained from this type of experiment is specifically referred to herein as the median paralysis unit (MPU).

(c) Determination of the $LD_{50}$:

Samples of botulinum neurotoxin were solubilized in 0.5 ml of sterile 0.2% type A gelatin in 30 mM sodium phosphate buffer, pH 6.20. As discussed earlier, gelatin is added to the buffer to stabilize preparations of botulinum neurotoxin. This resuspension was allowed to equilibrate for 15 minutes prior to dilution. The reconstituted neurotoxin was diluted into culture tubes containing 0.2% gelatin in 30 mM sodium phosphate buffer, pH 6.20, to give 4 dilutions that contained between 0.45 to 1.8 U of neurotoxin per 0.5 ml. Assays in which 25 or 50 mice were injected, 5 dilutions of toxin and 5 or 10 mice were used per dilution, respectively. Several different series of dilutions of neurotoxin were used and the ratio between successive doses was approximately 1.25. Dilutions were increased in approximately a geometric progression to achieve a symmetric design using well-known statistical methods similar to those described by Finney, D. J. (1978) *Statistical Method in Biological Assay* (Charles Griffin & Co., London). Ten dilutions were used for the 100 animal assays: the ratio of successive doses was 1.12 to 1.17. The dose range was between 0.6 and 1.6 units for the 50 and 25 animal assays. Diluted samples of neurotoxin were administered by i.p. injection to 18–22 g mice. Following injection the mice were observed for 4 days.

The percent death was determined at each dose of neurotoxin and probit analysis was performed on the data using the probit program described above. In keeping with conventional statistical practices, the 95% fudicial confidence intervals for the estimates of the $LD_{50}$ were determined using art-recognized methods similar to those described by Finney, D. J., (1971) *Probit Analysis* (3rd Ed.) University Press, Cambridge. Again, a Pearson chi-square goodness of fit test was used and if this estimate was significant, a heterogeneity factor was used in the calculation of the confidence limits.

EXAMPLE 2

The Effect Of The A And B Neurotoxins On Hind Limb And Paw Paralysis

CD1 (virus and antibody-free) white male mice (weighing 18–22 g) were obtained from Charles River Breeding Laboratories (Wilmington, Mass.). Type A porcine skin gelatin was obtained from Sigma Chemical Co. (St. Louis, Mo.).

FIG. 2 demonstrates the relationship between the effect of the A and B neurotoxins on the magnitude and duration of denervation. Paralysis of the mouse hind limb was produced by injection of 1 MPU of botulinum neurotoxin into the gastrocnemius muscle. Neurotoxin was diluted with 0.2% gelatin in 30 mM sodium phosphate buffer, pH 6.2 and 0.1 ml of serotype A (upper panel) or B (lower panel) neurotoxins were injected into the gastrocnemius muscle of the hind limb of 18–22 g mice. The percent of mice showing complete paw paralysis was determined over a total of 9 days. The results were obtained from a total of 11 experiments.

Paw paralysis (open bars, FIG. 2) was the first major effect observed following neurotoxin injection and preceded the onset of hind limb paralysis (solid bars, FIG. 2). Additionally, the effect on paw and complete hind limb paralysis was further distinguishable on the basis of the magnitude of effect and the duration of action. A maximum of 50% of the mice showed complete hind limb paralysis versus the 100% showing complete paw paralysis. Hind limb paralysis lasted for 4 to 5 days whereas paw paralysis lasted for 8 to 9 days. Paw paralysis appeared to be more sensitive to both the A and B toxins.

Figure 3:
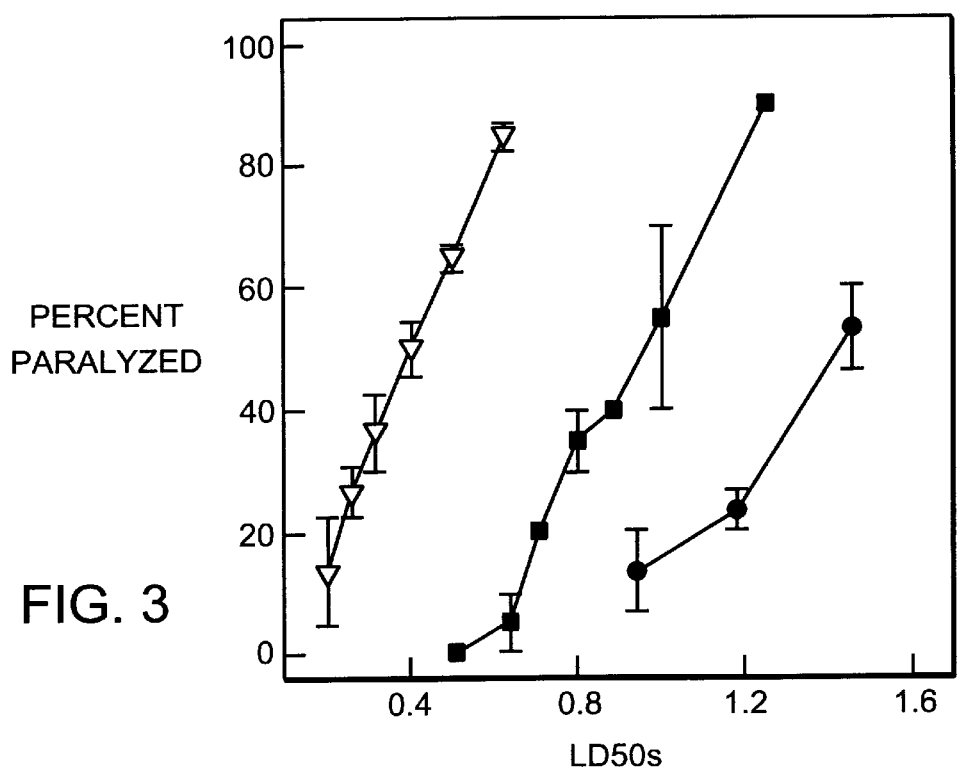
FIG. 3 is a dose-response curve illustrating the effect of A and B neurotoxins (alone and admixed) on complete hind limb paralysis using $LD_{50}$.
Figure 4:
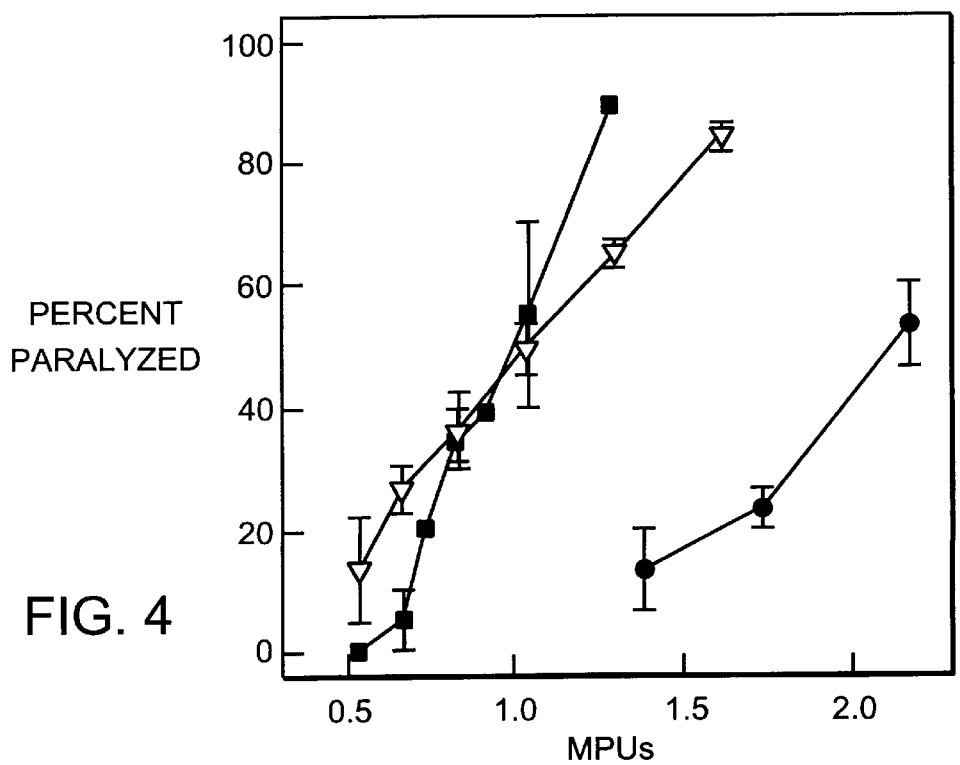
FIG. 4 is a dose-response curve illustrating the effect of A and B neurotoxins (alone and admixed) on complete hind limb paralysis using MPU.

Collectively, FIGS. 3 and 4 represent a comparison of the $LD_{50}$ versus MPU dose dependence of hind limb paralysis produced by the A and B serotypes of botulinum neurotoxin administered alone or admixed. The amount of neurotoxin activity in a given preparation was assessed by evaluating the percent of mice at each dose that showed complete paralysis of the hind limb. In FIG. 3, the doses of the neurotoxin preparations were expressed in terms of the number of $LD_{50}$s. The data shown in FIG. 3 indicate that the number of $LD_{50}$ units of the A serotype alone (open triangles) and the B serotype alone (solid squares) required to produce an equivalent effect on the mouse hind limb are different. More significantly, the admixture of the two neurotoxins (solid circles) did not result in a dose response curve somewhere in the middle of the two curves for A and B but, rather, produced a curve far to the right of the less potent B neurotoxin.

In FIG. 4, the effect of serotype A (open triangles), B (solid squares) or admixtures of A and B (solid circles) neurotoxins are presented (using the same data as presented in FIG. 3), however, the data are plotted in terms of the median paralysis unit (MPU). In this case, the curves for the A and B neurotoxins are superimposable. However, the curve for the admixture of the neurotoxins is again far to the right, indicating that the admixture was less potent with respect to complete hind limb paralysis.

Significantly, at all the doses at which complete hind limb paralysis was noted for the A and B neurotoxins alone, all (100%) of the animals showed complete paw paralysis. In contrast, in the case of the admixture of the A and B neurotoxins, complete paw paralysis was observed for all of the animals at all doses tested, but this occurred even in the absence of complete hind limb paralysis. Thus, at equivalent total units of activity, the effect of the admixture of A and B neurotoxins was primarily that of producing the more localized paw paralysis whereas the effect of the individual neurotoxins included paw paralysis and extended to the less localized, wider spread complete hind limb paralysis.

EXAMPLE 3

Duration Of Action Of Localized Denervation Produced By A And B Neurotoxins

CD1 (virus and antibody-free) white male mice (weighing 18–22 g) were obtained from Charles River Laboratories and type A porcine skin gelatin was obtained from Sigma Chemical Co.

Figure 5:
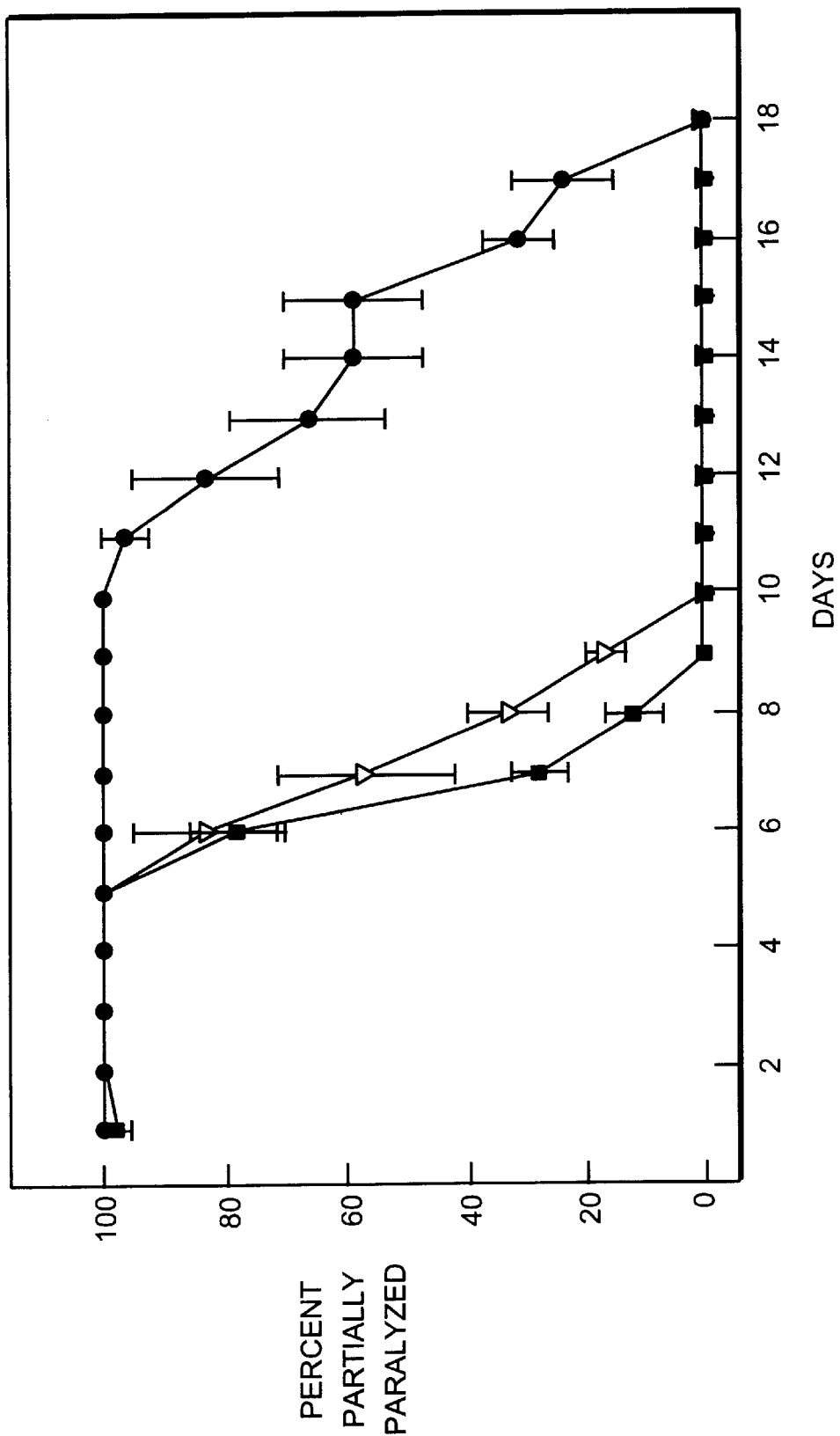
FIG. 5 is a graph depicting the duration (in days) of localized denervation (partial paralysis) using A and B neurotoxins (alone and admixed).

The duration of paw paralysis was examined following i.m. administration of A and B neurotoxins alone or admixed into the gastrocnemius muscle. The results of these studies are shown in FIG. 5. Neurotoxin was diluted with 0.2% gelatin in 30 mM sodium phosphate buffer, pH 6.2 and 0.1 ml of diluted neurotoxin preparations of A (open triangles), B (solid squares) and admixtures of A and B (solid circles) were injected into the gastrocnemius muscle of the hind limb of 18–22 g mice. The percent of mice showing paw paralysis (partial paralysis) was determined over a total of 18 days. The results were obtained from a total of three experiments.

The data obtained following administration of the A and B neurotoxins alone showed that the duration of action at 1.0 MPU was 9 and 8 days, respectively. When an admixture of the two neurotoxins totalling 2.0 MPUs was administered into the gastrocnemius muscle, the duration of action was 17 days. These observations indicate that the effect of admixing the A and B serotypes was to potentiate paw paralysis. Thus, when taken together with FIG. 4, two different measures of the denervating effects of neurotoxin, paw paralysis and complete hind limb paralysis, measured in the same limb gave very different results.

TABLE 1

| Neurotoxin Formulation | $LD_{50}$/MPU |
|---|---|
| A toxin | 0.39 |
| B toxin | 0.97 |
| A & B toxins | 1.35 |
| Dysport ® | 1.00 |
| Botox ® | 0.41 |

The above-described observations suggest that formulations of botulinum neurotoxin have distinct characteristics following injection into muscle as compared to their reported characteristics following i.p. injection. This is further illustrated in Table 1 which summarizes experiments in which different preparations and serotypes of botulinum toxin were compared. The biologic activity of each preparation has been expressed in terms of the number of $LD_{50}s$ that are equivalent to 1.0 MPU. These data show that significant differences have been observed in the number of $LD_{50}s$ required to produce an equivalent effect in the mouse hind limb. This confirms that the $LD_{50}$ does not predict the denervating efficacy of botulinum neurotoxin when injected into muscle. Clearly, only characterization by the MPU takes into consideration the tissue dependency of the efficacy of the botulinum toxin (See, e.g., Pearce et al. (1995), cited above and Pearce et al. (1994) cited above, the disclosures of which are hereby incorporated by reference). This also explains, in part, why the mouse hind limb bioassay is a better predictor of the differences in the potency of the clinical preparations of botulinum toxin, Botox® and Dysport®.

EXAMPLE 4

Differences Between Single And Admixed Doses Of Neurotoxins And The Clinical Significance Thereof As described above, the hind limb paralysis model indicates that different effects can be obtained following intramuscular injection of an admixture of A and B neurotoxins. Specifically, the admixture of the A and B neurotoxins was antagonistic with respect to hind limb paralysis when compared to that observed for either of the neurotoxins alone. At the same time, however, the admixture potentiated, i.e., was additive with respect to, paw paralysis. These different responses within the same tissue can be explained, in part, on the basis of our knowledge of the pharmacological properties of these neurotoxins. Not wishing to be bound by theory, a possible relationship between a tissue diffusion gradient model and the observed pharmacology is discussed below.

Because botulinum neurotoxin A or B has a high molecular weight and may exist in association with several other proteins resulting in complexes with molecular weights as high as 900,000, the diffusion of neurotoxin is probably limited to the extracellular fluid. Applying a simple model involving radial diffusion of neurotoxin within an extracellular compartment described by a cylinder, for example, one would predict that the highest concentrations of neurotoxin would occur at the source point. For example, at an injection of 1.0 MPU of neurotoxin A or B, a very sharp concentration gradient would eventually develop within tissue. At a radius of 1.0 centimeter, the maximum concentration would decline by a factor of >100. At a radius of 1.9 centimeters, the concentration would further decline by a factor of >400. In fact, this theoretical model is consistent with the observations of histochemical and morphometric analyses of muscle following single point injection of either botulinum type A or B neurotoxin (See, e.g., Borodic et al. (1992), *Botulinum and Tetanus Neurotoxins* (ed., B. R. DasGupta, Plenum Press, New York) pp. 623–645; Borodic et al. (1993), 9 *Opthalamic Plastic and Reconstructive Surgery* 3:182–190).

As disclosed herein, the response to injection of either the A or B neurotoxin alone into the gastrocnemius muscle is characterized by the greater sensitivity of paw paralysis than complete hind limb paralysis. It is unlikely that this difference in sensitivity is due to differences in the neurotoxin's affinity for receptors on the cholinergic nerve terminals innervating these different muscles. Rather, a diffusion gradient phenomenon provides a better explanation for the apparent differential sensitivity of these two effects of the neurotoxin when administered singly. If we assume that paw paralysis is due to a more localized effect of neurotoxin and complete hind limb paralysis requires diffusion of neurotoxin to extend to and involve the muscles of the upper thigh, the effect of the proposed concentration gradient becomes intuitively obvious.

Figure 6:
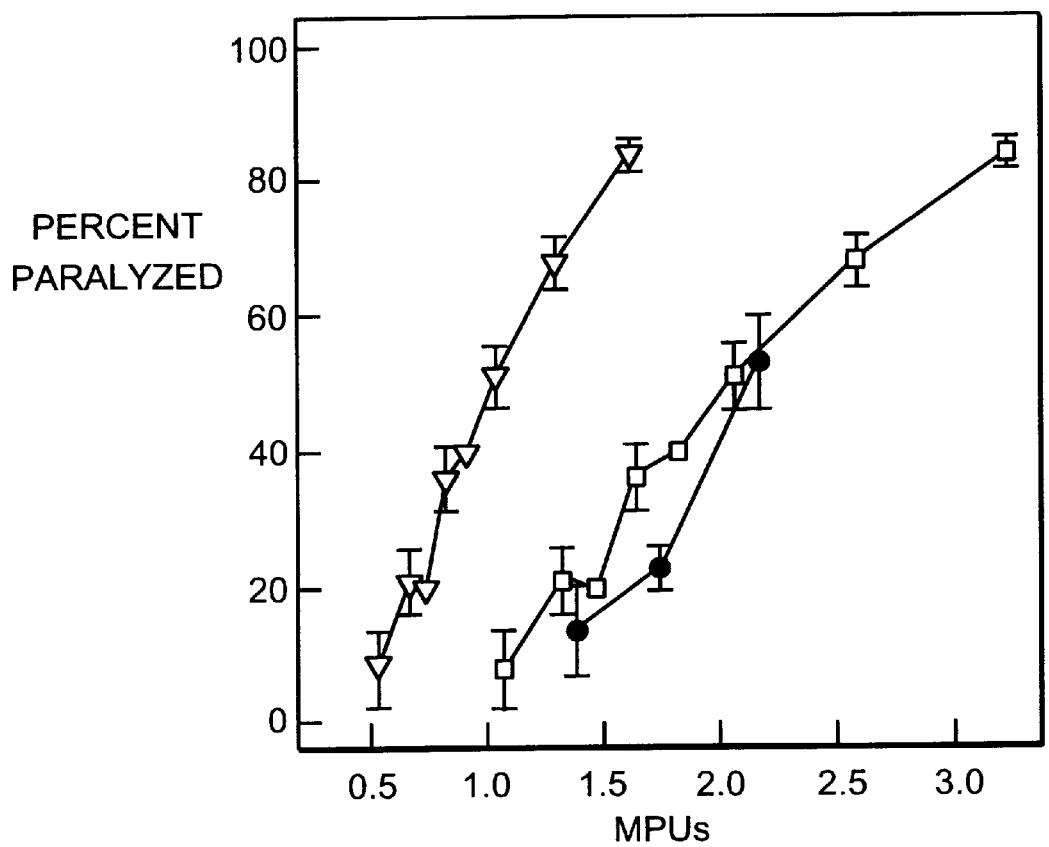
FIG. 6 is a dose-response curve illustrating denervating effects of varying dosages of admixtures of A and B neurotoxins as predicted by a diffusion gradient model.

The above-proposed diffusion model provides one plausible explanation for the effects produced following i.m. administration of either the A or B neurotoxin alone. While perhaps not immediately apparent, this same model can be applied to also explain the observed effects using an admixture of the A and B neurotoxins injected into the gastrocnemius muscle. On the one hand, the additive or potentiating effect on paw paralysis following i.m. injection is arguably predictable after-the-fact in view of the model proposed herein. On the other hand, the less than additive effect, i.e., antagonistic effect, on complete hind limb paralysis is not. In fact, the dose response curve for complete hind limb paralysis is exactly that anticipated for either one of the neurotoxins alone at half the dose of the admixture. This is illustrated in FIG. 6 in which the actual data observed following i.m. administration of the admixture of A and B neurotoxins (solid circles) on complete hind limb paralysis are compared against a theoretical curve (open squares). The curve on the left (open triangles) was obtained by averaging paralysis data obtained for the A and B neurotoxins alone. The theoretical curve (open squares) was obtained by shifting this curve of averages (open triangles) to the right by a factor of 2. Now, this average curve very closely predicts the observed response for the admixture of the A and B neurotoxins.

This phenomenon can be explained, in part, if it is assumed that the A and B neurotoxins interact with distinct receptors that do not, to any significant extent, recognize the other. Before botulinum neurotoxin can reach its site of action within the nerve terminal, it must first bind to the membrane receptor (acceptor) whereupon it enters the nerve terminal by a well-known process of receptor-mediated endocytosis. Assuming the model of radial diffusion proposed herein, the further from the point of injection the lower the concentration of neurotoxin. Thus, at some point the concentration of neurotoxin is too low to produce a detectable response. Thus, in the case where an admixture of A and B neurotoxins is injected, the receptors for the A and B neurotoxins only see the concentration of the individual neurotoxins and therefore the point within the diffusion gradient at which the admixture of the A and B neurotoxins no longer effectively bind to their respective receptors is unchanged compared to half the total dose of either the A or B neurotoxin alone. At the site of injection, occupancy theory predicts a 22% receptor occupancy, whereas at 1.2 centimeters from the site of injection only 0.22% are occupied while at 1.9 centimeters only 0.07% of receptors bind to neurotoxin. Thus, within the denervation field dictated by the affinity of the neurotoxin receptors and the concentration of the individual neurotoxins, the denervating effect of the two neurotoxins would arguably be predicted to be additive. Similarly, this approach arguably further predicts that, at equivalent doses of the A or B neurotoxins alone, the diffusion gradient would extend beyond that observed for the admixture of A and B neurotoxins. This is precisely what was observed experimentally and disclosed herein.

Thus, as disclosed herein, admixing different neurotoxins provides a means by which the denervating activity can be delimited and contained within a smaller field. As is well-documented in the prior art, the majority of side-effects associated with neurotoxin therapy are due to untoward spread of the denervation field. An ability to focus the effect of denervation as disclosed herein will provide significant advantages in the clinical setting.

Another advantage associated with the localized effect of the neurotoxin composition disclosed herein is an increase in the duration of chemodenervation. As indicated herein, 1.0 MPU of either the A or B neurotoxins alone produces paw paralysis that lasted for essentially the same amount of time, 8–9 days (FIG. 5) while a combination of 1.0 MPU of each of neurotoxin A and B resulted in paw paralysis for approximately 16–18 days (FIG. 5). This observation further suggests that it is probably possible, using the instant compositions and methods, to double the amount of neurotoxin that is normally given therapeutically, which in turn results in twice the duration of action of the toxin without the diffusion-related effects that would be observed with the equivalent number of units of one of the neurotoxins alone. Again, an ability to focus the effect of denervation coincident with the ability to prolong the effect of denervation as disclosed herein will provide significant advantages in the clinical setting.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. An improved pharmaceutical composition for localized chemodenervation, the composition comprising:
 an admixture of:
  (a) a first neurotoxin, said first neurotoxin having a diffusion gradient that defines a first denervation field associated with said first neurotoxin;
  (b) a second neurotoxin, said second neurotoxin being different from said first neurotoxin and having a diffusion gradient that defines a second denervation field associated with said second neurotoxin; and,
  (c) a pharmaceutically-acceptable excipient, where the neurotoxins are calibrated in median paralysis units and are admixed in amounts relative to each other such that they produce an additive therapeutic effect without untoward spread of either the first or the second denervation fields and the composition causes more localized, longer lasting denervation than either neurotoxin non-admixed.

2. The pharmaceutical composition of claim 1 wherein said first neurotoxin is selected from the group consisting of: C. botulinum serotype A, B, C, D, E, F, and G neurotoxins.

3. The pharmaceutical composition of claim 1 wherein said first neurotoxin is C. botulinum serotype A neurotoxin.

4. The pharmaceutical composition of claim 1 wherein said second neurotoxin is selected from the group consisting of: C. botulinum serotype A, B, C, D, E, F, and G neurotoxins.

5. The pharmaceutical composition of claim 1 wherein said second neurotoxin is C. botulinum serotype B neurotoxin.

6. The pharmaceutical composition of claim 5 wherein said C. botulinum serotype B neurotoxin is associated with botulinum-derived stabilizing proteins.

7. The pharmaceutical composition of claim 6 wherein at least one of said stabilizing proteins comprises a red blood cell agglutinating factor co-expressed with the neurotoxin by C. botulinum.

8. The pharmaceutical composition of claim 1 wherein said second neurotoxin is a tetanus neurotoxin.

9. The pharmaceutical composition of claim 1 wherein said combination further comprises at least a third neurotoxin wherein said third neurotoxin is different from either of said first or second neurotoxins.

10. The pharmaceutical composition of claim 1 wherein said pharmaceutically-acceptable excipient comprises a protein.

11. The pharmaceutical composition of claim 10 wherein said protein is selected from the group consisting of: albumin and gelatin.

12. The pharmaceutical composition of claim 1 in a form substantially free of water.

13. An improved pharmaceutical composition for localized chemodenervation, the composition comprising:
 an admixture of:
  (a) a first neurotoxin, said first neurotoxin comprising C. botulinum serotype A neurotoxin having a diffusion gradient that defines a fist denervation field associated with said C. botulinum serotype A; and,
  (b) a second neurotoxin, said second neurotoxin being different from said first neurotoxin and having a diffusion gradient that defines a second denervation field associated with said second neurotoxin,
 wherein the neurotoxins are calibrated in median paralysis units and are admixed in amounts relative to each other such that they produce an additive therapeutic effect without untoward spread of either the first or the second denervation fields and the composition causes more localized, longer lasting denervation than either neurotoxin non-admixed.

14. The pharmaceutical composition of claim 13 wherein said admixture further comprises a pharmaceutically-acceptable excipient.

15. An improved method for localized chemodenervation of a muscle, the method comprising the step of:

(a) administering to a muscle a dosage of a pharmaceutical composition sufficient to cause localized denervation, said composition comprising:
an admixture of:
(i) a first neurotoxin, said first neurotoxin having a diffusion gradient that defines a first denervation field associated with said first neurotoxin;
(ii) a second neurotoxin, said second neurotoxin being different from said first neurotoxin and having a diffusion gradient that defines a second denervation field associated with said second neurotoxin; and
(iii) a pharmaceutically-acceptable excipient, wherein the neurotoxins are calibrated in median paralysis units and are admixed in amounts relative to each other such that they produce an additive therapeutic effect without untoward spread of either the first or the second denervation fields and administering the composition causes more localized, longer lasting denervation than either neurotoxin non-admixed.

16. The method of claim 15 wherein step (a) comprises administering a unit dosage of the composition to an innervating zone within a volume of muscle, said volume comprising a single muscle.

17. An improved method for localized chemodenervation of a muscle, the method comprising the step of:
(a) administering to a muscle a dosage of a pharmaceutical composition sufficient to cause localized denervation, said composition comprising:
an admixture of
(i) a first neurotoxin, said first neurotoxin comprising C. botulinum serotype A neurotoxin having a diffusion gradient that defines a first denervation field associated with said C. botulinum serotype A; and,
(ii) a second neurotoxin, said second neurotoxin being different from said first neurotoxin and having a diffusion gradient that defines a second denervation field associated with said second neurotoxin,
wherein the neurotoxins are calibrated in median paralysis units and are admixed in amounts relative to each other such that they produce an additive therapeutic effect without untoward spread of either the first or the second denervation fields and administering the composition causes more localized, longer lasting denervation than either neurotoxin non-admixed.

18. The method of claim 17 wherein said step (a) comprises administering a unit dosage of the composition to an innervating zone within a volume of muscle, said volume comprising a single muscle.

19. An improved method of locally diminishing spasm and involuntary contraction in a muscle, the method comprising the step of
(a) administering into at least a portion of an innervation zone of a muscle a dosage of the pharmaceutical composition of claim 1,
such that administering said composition causes longer lasting diminishment of spasm and involuntary contraction than either neurotoxin non-admixed.

20. An improved method of locally diminishing tremor, rigidity, or spasticity in a muscle, the method comprising the step of:
(a) administering into at least a portion of an innervation zone of a muscle a dosage of the pharmaceutical composition of claim 1,
such that administering said composition causes longer lasting diminishment of tremor, rigidity, or spasticity than administering either neurotoxin non-admixed.

21. An improved pharmaceutical composition for localized chemodenervation, the composition comprising:
an admixture of:
(a) a first neurotoxin, said first neurotoxin having a diffusion gradient that defines a first denervation field associated with said first neurotoxin;
(b) a second neurotoxin, said second neurotoxin being different from said first neurotoxin and having a diffusion gradient that defines a second denervation field associated with said second neurotoxin; and,
(c) a pharmaceutically-acceptable excipient, wherein the neurotoxins are calibrated in median paralysis units and are admixed in amounts relative to each other such that they produce an additive therapeutic effect without untoward spread of either the first or the second denervation fields and the composition causes more localized denervation than either neurotoxin non-admixed.

22. An improved method for localized chemodenervation of a muscle, the method comprising the step of:
(a) administering to a muscle a dosage of a pharmaceutical composition sufficient to cause localized denervation, said composition comprising:
an admixture of
(i) a first neurotoxin, said first neurotoxin having a diffusion gradient that defines a first denervation field associated with said first neurotoxin;
(ii) a second neurotoxin, said second neurotoxin being different from said first neurotoxin and having a diffusion gradient that defines a second denervation field associated with said second neurotoxin; and,
(iii) a pharmaceutically-acceptable excipient,
wherein the neurotoxins are calibrated in median paralysis units and are admixed in amounts relative to each other such that they produce an additive therapeutic effect without untoward spread of either the first or the second denervation fields and administering the composition causes more localized denervation than either neurotoxin non-admixed.

23. An improved method for localized chemodenervation of a muscle, the method comprising the step of:
(a) administering to a muscle a dosage of a pharmaceutical composition sufficient to cause localized denervation, said composition comprising:
an admixture of
(i) a first neurotoxin, said first neurotoxin having a diffusion gradient that defines a first denervation field associated with said first neurotoxin;
(ii) a second neurotoxin, said second neurotoxin being different from said first neurotoxin and having a diffusion gradient that defines a second denervation field associated with said second neurotoxin; and,
(iii) a pharmaceutically-acceptable excipient,
wherein the neurotoxins are calibrated in median paralysis units and are admixed in amounts relative to each other such that they produce an additive therapeutic effect without untoward spread of either the first or the second denervation fields and administering the composition causes longer lasting denervation than either neurotoxin non-admixed.

* * * * *